United States Patent
Perovitch et al.

(10) Patent No.: US 8,889,663 B2
(45) Date of Patent: Nov. 18, 2014

(54) FORMULATION FOR ORAL TRANSMUCOSAL ADMINISTRATION OF LIPID-LOWERING DRUGS

(76) Inventors: Philippe Perovitch, Le Temple (FR); Marc Maury, Saint Medard en Jalles (FR)

( * ) Notice: Subject to any disclaimer, the term of this patent is extended or adjusted under 35 U.S.C. 154(b) by 26 days.

(21) Appl. No.: 13/141,597

(22) PCT Filed: Dec. 17, 2009

(86) PCT No.: PCT/FR2009/052591
§ 371 (c)(1),
(2), (4) Date: Jun. 22, 2011

(87) PCT Pub. No.: WO2010/072950
PCT Pub. Date: Jul. 1, 2010

(65) Prior Publication Data
US 2011/0257149 A1  Oct. 20, 2011

(30) Foreign Application Priority Data
Dec. 22, 2008  (FR) ........................ 08 58947

(51) Int. Cl.
*A61K 31/407* (2006.01)
*A61K 47/10* (2006.01)
*A61K 9/00* (2006.01)

(52) U.S. Cl.
CPC ............ *A61K 9/006* (2013.01); *A61K 47/10* (2013.01)
USPC .................................. 514/210.02

(58) Field of Classification Search
CPC ............... A61K 47/10; A61K 9/006
USPC .................................. 514/210.02
See application file for complete search history.

(56) References Cited

U.S. PATENT DOCUMENTS

| | | |
|---|---|---|
| 6,440,453 B1 | 8/2002 | Fischer et al. |
| 2005/0025714 A1* | 2/2005 | Dugger, III .............. 424/44 |
| 2005/0281868 A1 | 12/2005 | Lane |
| 2007/0225379 A1 | 9/2007 | Carrara et al. |
| 2008/0171089 A1* | 7/2008 | Blondino et al. .......... 424/489 |
| 2008/0249120 A1* | 10/2008 | Soni et al. ................ 514/275 |

FOREIGN PATENT DOCUMENTS

| | | |
|---|---|---|
| WO | 2006/119598 A2 | 11/2006 |
| WO | 2007/009320 A1 | 1/2007 |
| WO | 2008/079295 A1 | 7/2008 |

OTHER PUBLICATIONS

Manzoni M, Rollini M. Biosynthesis and biotechnological production of statins by filamentous fungi and application of these cholesterol-lowering drugs. Appl Microbiol Biotechnol. Apr. 2002;58(5):555-64. Epub Feb. 14, 2002.*

Y. S. R. Krishnaiah, et al., "Penetration-Enhancing Effect of Ethanolic Solution of Menthol on Transdermal Permeation of Ondansetron Hydrochloride Across Rat Epidermis", Drug Delivery, Jan. 1, 2008, pp. 227-237, vol. 15, No. 4, Academic Press, Orlando, FL., United States.

Koichi Takahashi, et al., "Novel approach to improve permeation of ondansetron across shed snake skin as a model membrane", Journal of Pharmacy and Pharmacology, Jun. 1, 2001, pp. 789-794, vol. 53, No. 6, Royal Pharmaceutical Society of Great Britain, Great Britain.

* cited by examiner

*Primary Examiner* — Paul Zarek
(74) *Attorney, Agent, or Firm* — Sughrue Mion, PLLC

(57) ABSTRACT

The invention relates to a formulation for delivering by oral transmucosal administration at least one lipid-lowering active principle, preferably from the statin family, said formulation including said active principle in the base or salt form, an aqueous alcohol solution titrating at least 30° alcohol, and optionally a pH correcting agent and/or an antioxidant, said active principle being in a stable and completely dissolved state in the aqueous alcohol solution. The invention also relates to a method of preparing said formulation and to the use thereof, preferably in single-dose packaging, for treating and preventing hyperlipemia and/or cardiovascular conditions.

6 Claims, No Drawings

FORMULATION FOR ORAL TRANSMUCOSAL ADMINISTRATION OF LIPID-LOWERING DRUGS

CROSS REFERENCE TO RELATED APPLICATIONS

This application is a National Stage of International Application No. PCT/FR2009/052591, filed on Dec. 17, 2009, which claims priority from French Patent Application No. 0858947, filed on Dec. 22, 2008, the contents of all of which are incorporated herein by reference in their entirety.

The present invention relates to a formulation for instantaneous systemic administration by the oral transmucosal route of at least one lipid-lowering drug active principle, in particular an active principle belonging to the statin family.

The invention also relates to a method of preparing this formulation and to its pharmaceutical use, in particular for treating hyperlipidemia and/or for preventing and treating cardiovascular conditions.

The global pharmaceuticals market is dominated by products intended to treat or prevent cardiovascular conditions. A significant proportion of these products contain lipid-lowering drug molecules intended to treat hyperlipidemia, including hypercholesterolemia.

Lipid-lowering drugs are pharmaceutically active principles capable of lowering the level of lipids in the blood and in particular of inhibiting the production of cholesterol. The primary function of some lipid-lowering drugs is to reduce endogenous synthesis of cholesterol in the liver by inhibiting the activity of HMG CoA reductase, a hepatic cell enzyme used in the synthesis of a cholesterol precursor, namely mevalonate.

There are various lipid-lowering drug active principles.

More particularly known are molecules from the statin family, notably atorvastatin, pravastatin, simvastatin, lovastatin, fluvastatin, and rosuvastatin.

Like all lipid-lowering drugs, statin molecules reduce the synthesis of cholesterol by inhibiting the activity of HMG CoA reductase, but they also have potential capacity for reducing atheromatous plaque at the arterial endothelium, thus preventing or attenuating ischemic syndromes. Moreover, long-term treatment using statins prevents to a significant degree the primary occurrence of myocardial infarctions and secondary relapse events after a first ischemic attack.

Also known are fibrates such as fenofibrate, emfibrozil, and ezetimibe that belong to another class. These molecules act mainly by reducing the digestive absorption of cholesterol via the intestinal wall, an absorption area known as "brush-border mucosa". In contrast, they have no effect on central hepatic synthesis of cholesterol and they therefore remain accessory or accompanying treatments for treatment with statins, with which they are generally prescribed simultaneously, in certain highly-specific cases.

Lipid-lowering drugs in general, and statins in particular, are conventionally administered orally.

Administration by intravenous injection has been experimented with, but although rapid and efficacious, it is not suitable for basic daily treatment of hypercholesterolemia or for preventing heart attacks. Administration by transfusion requires dedicated personnel and the use of special equipment. It is costly and too burdensome for patients, who seek the simplest and most readily available ambulatory treatment.

The best-known oral form of administration is enteral administration via pills or capsules.

However, lipid-lowering drugs, notably statins, have physico-chemical and pharmacological characteristics that make their systemic bioavailability and their activity problematic, some causing intolerance problems, mainly digestive and muscular problems, depending on the dose administered orally.

This is caused for the most part by the lipophilic or ampiphilic nature of these low molecular weight molecules that, when introduced into the digestive tract and the stomach, suffer from the so-called "digestive first pass" effect, i.e. deterioration and losses linked to the stomach environment or to variations in intestinal physiology. Stomach passage with a very acid pH followed by passage through the duodenum and the small intestine furthermore produces known physicochemical or enzymatic interference that may denature and degrade the absorption of the lipid-lowering drug molecules. Once absorbed, the intact residual fraction of the administered dose of lipid-lowering drug reaches the portal vein via the mesenteric venous network to end up at the hepatic lobules and the structures known as the Disse space, where they are subjected to a so-called "hepatic first pass" effect that causes their metabolisation and/or more or less intense deterioration, with the production of numerous metabolites, some of which are inactive or toxic and may contribute to side effects.

The real bioavailable dose of active principle is therefore low: only a residual part of the administered quantity reaches the liver to inhibit the activity of HMG CoA reductase and reduce endogenous synthesis of cholesterol. The bioavailability of these active principles also varies from person to person, both in terms of absorption time and in terms of absorbed active principle ratio.

For example, average known residual bioavailabilities are:
  for a 20 milligram (mg) or 40 mg dose of lovastatin or Simvastatin, around 5% of the administered dose;
  for a 20 mg or 40 mg dose of provastatin, around 17% of the administered dose; and
  for a 10 mg to 80 mg dose of atorvastatin, from 12% to 14% of the administered dose.

What is more, the time before the appearance of a plasmatic peak following taking them is relatively long, averaging one to two hours. Some statin molecules are dispersed in a very large volume in the organism, linked to their lipophilic character, with the result that a major part of the active principle is distributed in a large organ and tissue space, exceeding 600 liters (L) for atorvastatin. Thus it is clear that, given this intense volumetric dispersion mechanism, only a residual fraction of the active principle is liable to exert its pharmacological activity at the level of the hepatic cells.

Thus major problems occur.

A first problem is administering a sufficient dose of lipid-lowering drug to the patient, given the weight of the person and the dilution and dispersion of this active principle in the organism, so that enough of the only meaningfully active part that acts on the HMG CoA reductase is available to be efficacious.

A second problem is the latency time caused by metabolization and dispersion in the organism before the lipid-lowering drug molecule begins to act.

Another problem is the appearance of side effects and intolerance, mainly digestive and muscular intolerance, linked to certain metabolization products of the molecules administered.

Enteral administration of lipid-lowering drugs, which is the only route used at present, is therefore in no way satisfactory, and it is necessary to provide a form of administration offering better pharmacokinetic, pharmacological, and therapeutic efficiency.

Thus there remains a need for a galenic formulation that is simple to use, of relatively low cost, easily available, and relatively non-invasive, enabling administration of an immediately bioavailable quantity of lipid-lowering drugs without the problems of absorption and digestive metabolization, so as to be able to effect treatment or prevention quickly, efficaciously, continuously, and at an effect/dose ratio the most suited to hypercholesterolemia and/or cardiovascular conditions.

To address this need, the present invention proposes a lipid-lowering drug formulation making it possible to deliver to the organism directly and without delay just the required efficacious dose without bioavailability problems, with a dose/effect ratio as close as possible to the ideally appropriate fraction for the required pharmacological activity. This is a very specific galenic formulation making it possible to guarantee instantaneous transmucosal administration of at least one lipid-lowering drug and/or cardiovascular protection active principle, in particular an active principle from the statin family, comprising:

said lipid-lowering drug and/or cardiovascular protection active principle;
an aqueous alcohol solution consisting of water and ethanol titrating at least 30° alcohol, in which said active principle is present in a stable and completely dissolved state; and
optionally, a pH corrector agent and/or an antioxidant.

The invention also proposes a method of preparing this formulation and its use for treating hypercholesterolemia and/or preventing and/or treating a cardiovascular event.

The formulation of the invention advantageously makes it possible to obtain at the lowest possible dose the best lipid-lowering drug and/or cardiovascular prevention effect that can be obtained with a lipid-lowering drug and/or cardiovascular protector active principle. It allows instantaneous and complete oral transmucosal passage of a therapeutic preparation based on at least one lipid-lowering drug molecule, notably a statin, by preventing salivary dilution and swallowing and thus inopportune passage through the digestive tract. The statins are delivered quasi-instantaneously and directly to the liver via the arterial circulation network, serving as HMG CoA reductase inhibitors. They are distributed by a direct route and initially to the whole of the macro-arterial and micro-arterial vascular network that carries them, where, before any organic and tissue dispersion of said active principle in the organism and tissues, they can exercise their role of a potential atheromatosis reducer in direct contact with parietal lesions of the network.

Other features and advantages emerge from the following description of the invention, which concentrates on statins in particular, without this being limiting on the invention, but transposable to other lipid-lowering drug and/or cardiovascular protector active principles such as fibrates, e.g. fenofibrate, gemfibrozil, or ezetimibe.

Thus a first aspect of the invention provides a formulation for oral transmucosal administration of at least one lipid-lowering drug and/or cardiovascular protection active principle, in particular an active principle from the statin family, comprising:

said lipid-lowering drug and/or cardiovascular protection active principle in base form or in salt form;
an aqueous alcohol solution consisting of water and ethanol titrating at least 30° alcohol, in which said active principle is present in a stable and completely dissolved state; and
optionally, a pH corrector agent and/or an antioxidant.

The active principle is present in a stable and completely dissolved state in the aqueous alcohol solution, to enable rapid absorption of said active principle via the mucosa of the oral cavity.

The formulation of the invention preferably consists of the active principle(s), the aqueous alcohol solution consisting of water and ethanol, and optionally a pH corrector agent and/or an antioxidant.

The expression "lipid-lowering drug and/or cardiovascular protector active principle" refers to:

lipid-lowering active principles, i.e. any molecule capable of inhibiting HMG CoA reductase and acting against excess cholesterol and/or triglycerides in the blood;
cardiovascular protection active principles, i.e. any molecule capable of reducing cardiovascular risk, notably capable of reducing the risk of heart attack, the thickness of arterial and coronary atheromatous plaque, etc.;
active principles considered to have both lipid-lowering drug and cardiovascular protector effects, i.e. which, apart from their capacity to reduce hypercholesteremia significantly, are also capable of reducing cardiovascular risk, for example atorvastatin and pravastatin.

The pharmaco-therapeutic category to which a molecule belongs is that assigned to it in its Marketing Authorization (or Notice of Compliance).

The expression "transmucosal route" refers to any passive passage of a lipophilic or amphiphilic molecule through the mucosa of the tongue, under the tongue, of the gums, of the palate, of the cheek, or any other mucosa of the oral cavity.

The expression "stable and completely dissolved state" refers to a solution state rendering the active principle in the molecular and weakly ionized state in its solution medium, this solution state preventing any possibility of inopportune recrystallization. This stable and completely dissolved state may be monitored immediately on use of the formulation of the invention evaluating the visual appearance of the solution obtained (measurement of the degree of limpidity) and then at the level of the filtration residues (appearance or non-appearance of crystals), and finally in the medium-term and long-term during stability tracking tests at varying temperatures and relative humidities.

The expression "aqueous alcohol solution titrating X degrees alcohol" refers to a solution presenting a degree of alcohol equal to X, corresponding to the ratio between the volume of pure (100°) alcohol contained in the aqueous alcohol solution and the total volume of that solution. The degree of alcohol of the aqueous alcohol solution varies as a function of the degree of the alcohol used to form the solution and the water/alcohol ratio of the solution. For example, for 100° alcohol and a water/alcohol ratio of 50/50, the aqueous alcohol solution titrates 50° alcohol.

The expression "pH corrector agent" refers to any acid or base agent not degrading the physico-chemical characteristics of the active principle(s).

The pH corrector agent is preferably chosen from carbonates and bicarbonates of sodium, monosodium or disodium phosphates, triethanolamine, sodium hydroxide (NaOH) and potassium hydroxide (KOH) and also hydrochloric, sulfuric, phosphoric, citric, malic, lactic, succinic, and/or butyric acid agents The expression "antioxidant" refers to an agent that prevents the loss of one or more electrons by a molecule, sometimes accompanied by a loss of protons (H+). The antioxidant is preferably chosen from vitamins E, C.

The lipid-lowering drug and/or cardiovascular protector active principle is present in base form or in salt form.

When the active principle is present only in base form, the formulation of the invention preferably contains an acid pH corrector agent.

When the active principle is present only in salt form, for example in succinate, hydrochloric, or sulfate form, the formulation of the invention preferably contains a base pH corrector agent.

In a highly preferred embodiment, the active principle is present in base form. The lipid-lowering drug molecules in base form, in particular statins in base form, being of lower molecular weight than those in salt form, dissolve and stabilize more easily in the formulation of the invention and are better suited to faster oral transmucosal passage.

The active principle may be chosen in particular from molecules of the statin family, such as atorvastatin, pravastatin, simvastatin, lovastatin, fluvastatin or rosuvastatin. The active principle is preferably base atorvastatin, base simvastatin, base lovastatin, mevastatin, or base pitavastatine. It may equally consist of fibrates, for example fenofibrate, gemfibrozil, or ezetimibe.

The formulation of the invention preferably takes the form of an aqueous alcohol solution containing from 30% to 90% by volume ethanol, and 10% to 70% by volume water. The formulation of the invention even more preferably takes the form of an aqueous alcohol solution containing from 40% to 85% by volume ethanol and 15% to 60% by volume water.

The aqueous alcohol solution has a variable degree of alcohol of at least 30°, preferably 30° to 70°, even more preferably 40° to 70°, and ideally 45° to 65°.

The aqueous alcohol solution is advantageously the only solvent used in the formulation of the invention.

Furthermore, the alcohol in the aqueous alcohol solution serves not only as a diluent for molecules that are insoluble in water but also to promote faster transmucosal absorption, at a rate that increases as a function of the degree of alcohol used. The degree of alcohol of the formulation must nevertheless not exceed 70° because a higher degree would be incompatible with a pharmaceutical product for oral application because it could burn the mucosa. By way of illustration, the dissolution coefficient of a statin in ethanol makes it possible to obtain complete dissolution of said active principle as high as 2 mg of statins per 0.75 milliliter (mL) of approximately 50° ethanol. This coefficient may be modulated as a function of the required alcohol dose, the degree of alcohol and the water/ethanol ratio used.

The pH of the formulation of the invention is preferably in the range 5.0 to 9.0, more preferably in the range 5.5 to 7.5. These pH values are favorable to optimum absorption of the solution.

The formulation of the invention enables the active principle to cross the oral mucosa passively within a few seconds of administration. This very fast absorption makes it possible to prevent stagnation of the solution and the active principle in the oral atmosphere and their inopportune mixing with saliva, which is liable to degrade them, and which would break the continuity and the stability of dissolution of the active principle(s). This short delay also makes it possible to prevent reflex swallowing of the solution and the active principle that it contains.

The transmucosal passage of the active principle presented in the solution state of the invention to the external epithelial membrane, consisting of phospho-lipid structures that absorb passively by elective affinity the lipophilic molecules present in the stable and completely dissolved state, is based on osmotic or pulling pressure toward the other side of said membrane, in which the concentration of dissolved active principle and the degree of the alcohol solution concerned both participate. The activity and strength of the osmotic pressure increase with the degree of alcohol that serves as absorption promoter. There is therefore a powerful two-fold osmotic effect that is produced both by the high degree of the alcohol in the formulation and also by the high and highly localized concentration of the dissolved active principle in contact with the mucosa.

In particular with lipid-lowering drugs, in particular statins, an appropriate degree of alcohol is in the range 40° to 70°, preferably in the range 45° to 65°. This makes it possible to obtain and simultaneously adjust the best coefficient of dissolution and stabilization of the molecules and to promote transmucosal passage with a delay of 4 seconds (s) to 6 s.

One particularly suitable embodiment corresponds to 1.0 mL of aqueous alcohol solution with a degree of alcohol of approximately 50° or 65° for 1 mg or 4 mg of statins.

The mucosa of the mouth have a very dense, quasi-spongy array of micro-vessels, so that the molecules of the alcohol solvent and the dissolved active principle, which pass through the lipophilic pores of the epithelial membrane, are instantly captured by the sublingual veins and those draining the oral mucosa and conveyed to the jugular veins, and from there to superior vena cava and the right-hand side of the heart. The lipid-lowering drug molecules are then sent from the left-hand side of the heart into the systemic arterial vascular tract, which distributes them directly and without delay to the hepatic cells. The lipid-lowering drug molecules therefore reach the hepatocyte cells in the same nutrient and oxygenating blood flow indispensable to their metabolic life. Furthermore the passage of the lipid-lowering drug active principles in contact with the arterial endothelial tissue contributes to the anti-atheromatous and anti-ischemic activity of some of them.

This phenomenon is accentuated by the presence of the alcohol, which causes vasodilation with a local increase in the micro-vascular flow of the mucosa in direct contact with the formulation. Because of this locally high micro-circulation flow, there is never equilibrium on either side of the epithelial membrane: the concentration at its external surface, in the mouth, always remains very high, until exhaustion of the mechanism for want of molecules to absorb.

Use of the galenic formulation of the invention makes it possible to administer passively a dose of lipid-lowering drugs, and in particular of statins, that is absorbed immediately on deposition in contact with the mucosa, to be distributed instantly by the vascular route, with no delay for its pharmacological action, and without first suffering the destructive effects of digestive and hepatic passage. The galenic formulation of the invention therefore enables immediate and complete absorption by the tissue of the lipid-lowering drug molecules contained in the formulation, followed by their distribution in the central circulation of the organism, generating a rapid "flash" type pharmacological response.

For example, with a galenic formulation of the invention prepared from 2 mg of a base statin dissolved in 1.0 mL of a 50° ethanol solution, there may be administered passively and quasi-instantaneously a very significant dose of active principle that is conveyed directly by the arteries to the liver, to the very heart of the hepatic cells, where it exercises its HMG CoA reductase antagonist function. This 2 mg dose is at least equivalent to that obtained and recognized as bioavailable and therefore effective for administration by the enteral route, i.e. at best 5% to 20% of the dose usually administered, depending on the statins concerned. With the formulation of the invention, the bioavailability of the dose delivered by oral transmucosal administration is equivalent or very close to that obtained by the oral route after digestive absorption and metabolization of high doses.

The aqueous alcohol solution of the invention, titrating at least 30° alcohol, also has the advantage of dissolving lipid-lowering drug molecules, in particular statin molecules, although they are lipophilic or amphiphilic, which allows their spontaneous absorption via the oral mucosa, which are also lipophilic and selective, and protects the pharmaceutical formulation against microbiological contamination without having to introduce antibiotic preservatives.

Thus the aqueous alcohol solution of the invention has a four-fold efficacy:
  it serves as a solvent for the lipid-lowering drug active principle, in particular one from the statin family, which are lipophilic or amphiphilic molecules of low molecular weight, maintaining it in a state of stable and perfect dissolution;
  it activates transmucosal passage of this dissolved active principle presented in the molecular state in this way at the level of the lipophilic oral mucous membrane;
  the degree of alcohol increases the rate of transmucosal absorption in two ways, by osmotic effect and by causing reflex micro-vascular vasodilation, which accelerates the local micro-circulatory flow; and
  it is its own stability agent, which avoids the use of conventional additives.

The present invention advantageously offers very simple production and very good galenic stability: the extremely simplified water/alcohol solution guarantees dissolution of the active principle and makes it possible to dispense with most of the excipients normally used for conventional pharmaceutical preparations, including preservatives.

Thus it makes it possible to reduce production costs and at the same time to reduce the risks of intolerance and possible interaction between active principle and excipients.

Another advantage is that there is a very short delay in the pharmacodynamic action of the galenic formation of the invention compared to the slow absorption of existing lipid-lowering drug medications, which takes from one to two hours after administration by the oral digestive route.

The quasi-instantaneous vascular delivery proposed by the invention is entirely suitable for treating hypolipemia and hypercholesterolemia and preventing and/or treating cardio-vascular conditions. It can make it possible for a patient himself or herself to administer a product corresponding by weight to just what is really bioavailable via the oral route, equivalent to the efficacy of flash intravenous injection, without the drawbacks that render this type of administration unacceptable and inconceivable for uninterrupted basic treatment of tens of millions of patients.

It is an administration route that is much better in terms of simplicity and of non-traumatic administration availability, and also in terms of attractive unit and therapeutic costs compared to existing lipid-lowering drug administration methods.

The improvement in terms of dose/effect ratio is at least 70% to 95%. With the formulation of the invention, an at least 70% to 95% lower dose is used to obtain a therapeutic effect without delay. The lipid-lowering drug modules administered encounter no significant obstacle to their instantaneous distribution via the arteries to the hepatic cells, which they reach in a few seconds, so that the basic dose administered is considerably reduced compared to the recognized bioavailable dose indispensable for exercising the required pharmacological activity of lipid-lowering drugs. This dose is of course dependant on the required effect. It is preferably in the range 2 mg to 8 mg of active principle for volumes of aqueous alcohol solution in the range 0.2 mL to 2 mL. The dose is preferably in the range 2 mg to 4 mg for each 1.0 mL of aqueous alcohol solution.

Moreover, the oral mucosa having an extremely large total absorption area, demultiplied by its creased villous tissue character, administration of the formulation of the invention is free of all risk of untimely swallowing or misrouting. It enables extremely fast transmucosal passage, which limits mixing with alcohol and swallowing of the administered active principle, with the advantage of not destabilizing the mucosa with various elements or excipients, as is the case with some existing formulations.

Moreover, the effects of the alcohol are insignificant. For example, 0.75 mL of a 50° ethanol aqueous alcohol solution could only result in a alcohol blood level below 0.005 grams (g) per liter of blood, according to the official Widmark reference formula, i.e. one hundredth of the legal tolerance in France, which is set at 0.5 g per liter of blood. Moreover, the initial pulmonary expulsion of the alcohol solution has to allow virtually complete elimination of the ethanol in the form of vapor extracted via the respiratory route and exhaled before the ethanol can be distributed in the organism. The alcohol vector is thus eliminated almost completely via the respiratory parenchyma.

A second aspect of the invention relates to a method of preparing the formulation.

A particularly suitable method of producing the galenic formulation of the invention comprises the following steps:
  mixing alcohol and purified water and introducing into this mixture at least one lipid-lowering drug active principle, for example at least one active principle from the statin family;
  optionally introducing an antioxidant;
  stirring the preparation until a homogeneous suspension is obtained;
  optionally and progressively introducing a pH corrector agent until the required pH in the range 5.0 to 8.0 is obtained;
  further stirring until complete dissolution of the active principle;
  adding water if, necessary to make up to the required volume; and
  filtering.

The ethanol used may be absolute ethanol. It is preferably 95° ethanol.

In a preferred implementation, the method comprises the following steps:
  mixing ethanol and purified water and introducing into this mixture a lipid-lowering drug, preferably one from the statin family, in base or salt form;
  optionally introducing an antioxidant;
  stirring the preparation, preferably for 10 minutes (min) to 60 min, until a homogeneous suspension is obtained;
  optionally and progressively introducing a pH corrector agent until a required pH in the range 5.0 to 8.0 is obtained;
  further stirring, preferably for 5 min to 30 min, until complete dissolution of the active principle;
  adding water if necessary to make up to the required volume; and
  filtering.

In a first variant, the method of the invention comprises the following steps:
  mixing ethanol and water and introducing into this mixture a lipid-lowering drug active principle, preferably one from the statin family, in base form;

optionally introducing an antioxidant;
stirring the preparation, preferably for 10 min to 60 min, until a homogeneous suspension is obtained;
progressively introducing an acid pH corrector agent until a pH in the range 5.0 to 7, preferably close to 6.0, is obtained;
further stirring, preferably for 5 min to 30 min, until complete dissolution of the active principle;
adding water if necessary to make up to the required volume; and
filtering using a 5 µm filter and dispensing the preparation into single-dose bottles.

In a second variant, the method of the invention comprises the following steps:
mixing ethanol and water and introducing into this mixture a lipid-lowering drug active principle, preferably one from the statin family, in salt form;
optionally introducing an antioxidant;
stirring the preparation, preferably for 10 min to 60 min, until a homogeneous suspension is obtained;
progressively introducing a basic pH corrector agent until a pH in the range 6.0 to 8.0, preferably close to 7.0, is obtained;
further stirring, preferably for 5 min to 30 min, until complete dissolution of the active principle;
adding water if necessary to make up to the required volume; and
filtering using a 5 µm filter and dispensing the preparation into single-dose bottles.

The present invention may be used for instantaneous systemic transmucosal administration at lower and useful doses of lipid-lowering drugs and/or cardiovascular protectors, notably statins, for example atorvastatin, pravastatin, lovastatin or simvastatin.

The formulation of the present invention may in particular be used to produce a medication for treating hyperlipemia and/or preventing and/or treating heart conditions. Such a medication exhibits therapeutic activity in a very short time and at administered doses very much lower than the conventional doses.

The invention is therefore aimed at the use of the formulation for the production of a medication intended for treating hyperlipemia via the oral transmucosal route and at use of the formulation for the production of a medication for oral transmucosal administration to prevent and/or treat cardiovascular conditions.

The very small liquid volume of the formulation of the invention is very easy to administer. A patient may easily place it in their mouth in direct contact with a precise but smaller area of mucosa of the mouth, across the gums, or under the tongue.

According to a final aspect of the invention the formulation requires specific industrial packaging in order to allow its safe, simple and ergonomic use and to prevent the active principle from being degraded by contact with air as well as loss of degrees of alcohol.

One particular implementation consists in using an opaque glass or flexible metal-plastic or plastic packaging, preferably of small size, filled in an inert atmosphere such as nitrogen, to protect the stability of the composition and impermeability to oxygen and to radiation. These forms of packaging guarantee dissolution and stability over time of the dissolved active principles in hydro-alcohol solution of the invention.

These forms of packaging preferably include a cannula allowing precise deposition of the solution of the invention in contact with an appropriate area of the mucosa.

For comfortable use by the patient, for easy transportation, dedicated sealed packages may preferably be used for packaging. Even more preferably, the galenic form of the invention is packaged in single-dose packages of 0.5 mL to 2 mL, able to provide an adequate dose of active principle.

This packaging is advantageously easy to transport and allows easy use of the galenic formulation at any time of day.

Examples of formulations of statins of the invention may be mentioned, with a volume of 0.75 mL or 1.00 mL, using approximately 50° alcohol, particularly suited to producing effective cholesterol synthesis inhibiting action at the level of the hepatic system with a delay of only a few minutes:

FORMULATION 1

1 mg Atorvastatin, 1.0 mL of 50° Alcohol base atorvastatin (active principle): 1.0 mg
95° ethanol (diluent and absorption promoter): 0.5 mL
purified water (diluent): qsp 1.0 mL This first formulation example may be produced using the method described below for a batch of 1000 doses, i.e. 1.0 L.

Into a stainless steel tank introduce 0.5 L of 95% V/V ethanol and 0.5 L of purified water.

Introduce into the aqueous alcohol solution 1 g of base atorvastatin.

Using a helical stirrer, stir the preparation for 20 min to 40 min until a homogeneous suspension is obtained.

Continue stirring until complete dissolution.

Filter the preparation using a 5 µm polypropylene or like filter and dispense the preparation into 1.2 mL single-dose bottles.

FORMULATION 2

5 mg Atorvastatin, 1.2 mL of 50° Alcohol base atorvastatin (active principle): 5.0 mg
95° ethanol (diluent and absorption promoter): 0.6 mL
purified water (diluent): qsp 1.2 mL
hydrochloric acid (pH corrector): qsp pH 6.0

This second formulation example may be produced using the method described below for a batch of 1000 doses, i.e. 1.2 L.

Into a stainless steel tank introduce 0.6 L of 95% V/V ethanol and 0.25 L of purified water.

Introduce into the aqueous alcohol solution 5 g of base atorvastatin.

Using a helical stirrer, stir the preparation for 20 min to 40 min until a homogeneous suspension is obtained.

Then introduce hydrochloric acid progressively until a pH close to 6 is obtained (plus or minus 1).

Continue stirring until complete dissolution.

Make up with purified water to obtain a solution of 1.2 L volume and stir the preparation for 10 min to 30 min to ensure its homogeneity.

Filter the preparation on a 5 µm polypropylene or like filter and dispense the preparation into 1.2 mL single-dose bottles.

FORMULATION 3

2 mg Lovastatin, 1.0 mL of 50° Alcohol base lovastatin: 2.0 mg
95° ethanol: 0.5 mL
purified water: qsp 1 mL This formulation example may be produced using the method described below for a batch of 1000 doses, i.e. 1 L.

Into a stainless steel tank introduce 0.5 L of 95% V/V ethanol and 0.5 L of purified water.

Introduce into the aqueous alcohol solution 2 g of base lovastatin.

Using a helical stirrer, stir the preparation for 20 min to 40 min until a homogeneous suspension and complete dissolution are obtained.

Filter the preparation on a 5 µm polypropylene or like filter and dispense the preparation into 1.0 mL single-dose bottles.

FORMULATION 4

4 mg Lovastatin, 1.0 mL of 65° Alcohol base lovastatin (active principle): 4.0 mg
95° ethanol (diluent and absorption promoter): 0.65 mL
purified water (diluent): qsp 1.0 mL
HCl (pH corrector): qsp pH 7.0

This formulation example may be produced using the method described below for a batch of 1000 doses, i.e. 1.0 L.

Into a stainless steel tank introduce 0.650 L of 95% V/V ethanol and 0.350 L of purified water.

Introduce into the aqueous alcohol solution 4 g of base lovastatin.

Using a helical stirrer, stir the preparation for 20 min to 40 min until a homogeneous suspension is obtained.

Then introduce hydrochloric acid progressively until a pH close to 7 is obtained (plus or minus 1).

Continue stirring until complete dissolution.

Filter the preparation on a 5 µm polypropylene or like filter and dispense the preparation into 1.0 mL single-dose bottles.

FORMULATION 5

2 mg Simvastatin, 1.0 mL of 65° Alcohol base simvastatin (active principle): 2.0 mg
95° ethanol (diluent and absorption promoter): 0.65 mL
purified water (diluent): qsp 1.0 mL
HCl (pH corrector): qsp pH 7.0
vitamin E TPGS (antioxidant): 0.2 mg This formulation example may be produced using the method described below for a batch of 1000 doses, i.e. 1.0 L.

Into a stainless steel tank introduce 0.650 L of 95% V/V ethanol and 0.350 L of purified water.

Introduce into the aqueous alcohol solution 2 g of base simvastatin and 0.2 mg of vitamin E TPGS.

Using a helical stirrer, stir the preparation for 20 min to 40 min until a homogeneous suspension is obtained.

Then introduce hydrochloric acid progressively until a pH close to 7.0 is obtained (plus or minus 1).

Continue stirring until complete dissolution.

Filter the preparation on a 5 µm polypropylene or like filter and dispense the preparation into 1.0 mL single-dose bottles.

FORMULATION 6

4 mg Simvastatin, 1.2 mL of 65° Alcohol base simvastatin (active principle): 4.0 mg
95° ethanol (diluent and absorption promoter): 0.80 mL
purified water (diluent): qsp 1.2 mL
HCl (pH corrector): qsp pH 7.0
vitamin E TPGS (antioxidant): 0.2 mg This final formulation example may be produced using the method described below for a batch of 1000 doses, i.e. 1.2 L.

Into a stainless steel tank introduce 0.800 L of 95% V/V ethanol and 0.200 L of purified water.

Introduce into the aqueous alcohol solution 4 g of base simvastatin and 0.2 mg of vitamin E TPGS.

Using a helical stirrer, stir the preparation for 20 min to 40 min until a homogeneous suspension is obtained.

Then introduce hydrochloric acid progressively until a pH close to 7.0 is obtained (plus or minus 1).

Continue stirring until complete dissolution.

Make up with purified water to obtain 1.2 L of solution and stir the preparation for 10 min to 30 min to ensure its homogeneity.

Filter the preparation on a 5 µm polypropylene or like filter and dispense the preparation into 1.2 mL single-dose bottles.

Of course, the invention is obviously not limited to the examples described above, and on the contrary covers all variants, in particular with regard to the nature of the lipid-lowering drugs.

The invention claimed is:

1. A formulation for oral transmucosal administration of at least one lipid-lowering drug and/or cardiovascular protection active principle, the formulation comprising:
    said lipid-lowering drug and/or cardiovascular protection active principle, the dose of said active principle being less than 8 mg, wherein the active principle is selected from the group consisting of statins, fibrates and ezetimibe;
    an aqueous alcohol solution based on water and ethanol titrating between 45° and 65° ethanol, in which said active principle is present in a stable and completely dissolved state, the volume of said aqueous alcohol solution being less than 2 mL, and said aqueous alcohol solution being the only solvent in said formulation; and
    wherein the pH of the formulation is between 5.5 to 7.5.

2. The formulation according to claim 1, comprising a pH corrector agent selected from the group consisting of sodium carbonates and bicarbonates, monosodium or disodium phosphates, triethanolamine, sodium hydroxide, potassium hydroxide and hydrochloric, sulfuric, succinic, butyric, phosphoric, citric, malic and lactic acid agents.

3. The formulation according to claim 1, comprising an antioxidant selected from the group consisting of vitamin E and vitamin C.

4. The formulation according to claim 3, wherein the active principle is in base form and the pH corrector agent is an acid agent.

5. The formulation according to claim 3, wherein the active principle is in salt form and the pH corrector agent is a basic agent.

6. The formulation according to claim 1, wherein the active principle is mevastatin.

\* \* \* \* \*